(12) United States Patent
Victor et al.

(10) Patent No.: US 10,405,872 B2
(45) Date of Patent: Sep. 10, 2019

(54) CUTTING HEAD FOR AN INTRAMEDULLARY REAMER

(71) Applicant: Greatbatch Ltd., Clarence, NY (US)

(72) Inventors: Gary C. Victor, Wheatfield, NY (US); Kari Ann Sausen, Clarence, NY (US); Jack T. Bryant, Winona Lake, IN (US)

(73) Assignee: VIANT AS&O HOLDINGS, LLC, Tempe, AZ (US)

( * ) Notice: Subject to any disclaimer, the term of this patent is extended or adjusted under 35 U.S.C. 154(b) by 275 days.

(21) Appl. No.: 15/676,228

(22) Filed: Aug. 14, 2017

(65) Prior Publication Data

US 2018/0042618 A1    Feb. 15, 2018

Related U.S. Application Data

(60) Provisional application No. 62/374,896, filed on Aug. 14, 2016.

(51) Int. Cl.
*A61B 17/16* (2006.01)
*A61B 17/00* (2006.01)

(52) U.S. Cl.
CPC ........ *A61B 17/164* (2013.01); *A61B 17/1615* (2013.01); *A61B 17/1617* (2013.01); *A61B 17/1633* (2013.01); *A61B 17/1628* (2013.01); *A61B 2017/0023* (2013.01);
(Continued)

(58) Field of Classification Search
CPC .............. A61B 17/164; A61B 17/1615; A61B 17/1617; A61B 17/16
See application file for complete search history.

(56) References Cited

U.S. PATENT DOCUMENTS

| 4,706,659 A | 11/1987 | Matthews et al. |
| 4,751,922 A | 6/1988 | Dipietropolo et al. |
| 5,122,134 A | 6/1992 | Borzone et al. |

(Continued)

FOREIGN PATENT DOCUMENTS

| CN | 201862859 | 6/2011 |
| EP | 2668931 | 12/2013 |

(Continued)

OTHER PUBLICATIONS

Partial European Search report, Application No. 17155887.7, dated Jun. 6, 2017.

(Continued)

*Primary Examiner* — Christian A Sevilla
(74) *Attorney, Agent, or Firm* — Steven J. Grossman; Grossman Tucker Perrault & Pfleger, PLLC

(57) ABSTRACT

A cutting head for use with an intramedullary reamer is described. The reamer cutting head is of a unitary body construction that comprises a conically-shaped body having a bone cutting portion spaced from a barrel portion for attachment to a drive shaft. The bone cutting portion comprises a plurality of blades having a tissue cutting edge that outwardly extends from the cylindrical body. The plurality of blades is positioned about the cutting head in a spaced apart manner. The various plurality of blades are arranged at prescribed angular relationship that increases cutting efficiency and debris removal, thereby reducing reactive torque, axial loading, and head pressure during a surgical procedure.

30 Claims, 9 Drawing Sheets

(52) U.S. Cl.
CPC .............. *A61B 2017/00477* (2013.01); *A61B 2017/00526* (2013.01); *A61B 2017/00982* (2013.01)

(56) References Cited

U.S. PATENT DOCUMENTS

| | | | |
|---|---|---|---|
| 5,968,048 | A | 10/1999 | Harder |
| 5,975,811 | A | 11/1999 | Briese et al. |
| 6,258,093 | B1 | 7/2001 | Edwards et al. |
| 6,918,913 | B2 | 7/2005 | White et al. |
| 6,949,101 | B2 | 9/2005 | McCleary et al. |
| 7,229,457 | B2 | 6/2007 | Murphy et al. |
| 7,803,159 | B2 | 9/2010 | Perez-Cruet et al. |
| 8,454,608 | B2 | 6/2013 | White et al. |
| 2004/0199166 | A1* | 10/2004 | Schmieding ....... A61B 17/1617 606/79 |
| 2004/0236339 | A1 | 11/2004 | Pepper et al. |
| 2005/0075638 | A1 | 4/2005 | Collazo et al. |
| 2006/0015110 | A1 | 1/2006 | Pepper et al. |
| 2007/0250067 | A1* | 10/2007 | Schmieding ....... A61B 17/0401 606/96 |
| 2008/0132929 | A1 | 6/2008 | O'Sullivan et al. |
| 2011/0144649 | A1 | 6/2011 | Victor et al. |
| 2012/0253348 | A1 | 10/2012 | Arlettaz et al. |
| 2015/0119893 | A1* | 4/2015 | Witt ..................... A61B 17/164 606/85 |
| 2017/0231643 | A1 | 8/2017 | Victor et al. |

FOREIGN PATENT DOCUMENTS

| | | |
|---|---|---|
| WO | 9849948 | 11/1998 |
| WO | 200143650 | 6/2001 |
| WO | 2011113115 | 9/2011 |
| WO | 2014075990 | 5/2014 |
| WO | 2017042914 | 3/2017 |

OTHER PUBLICATIONS

International Search Report, Application No. PCT/US17/46746 dated Nov. 2, 2017.

* cited by examiner

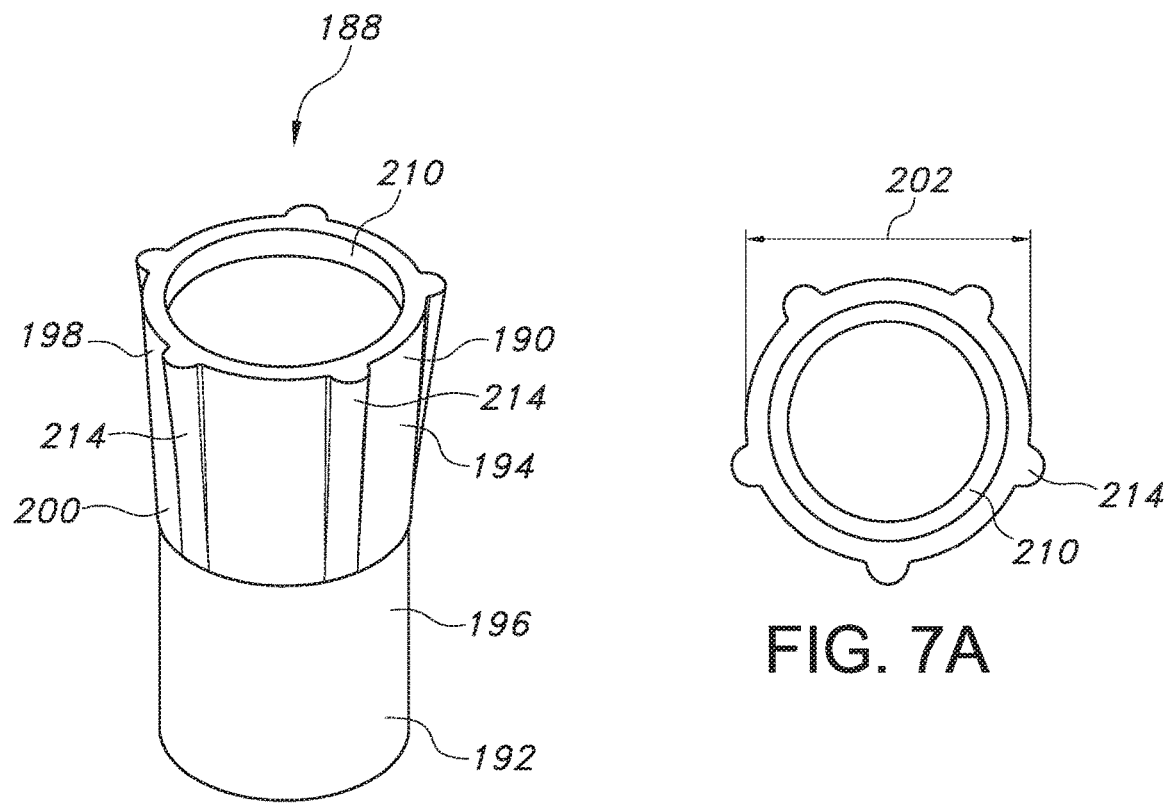
FIG. 7
FIG. 7A
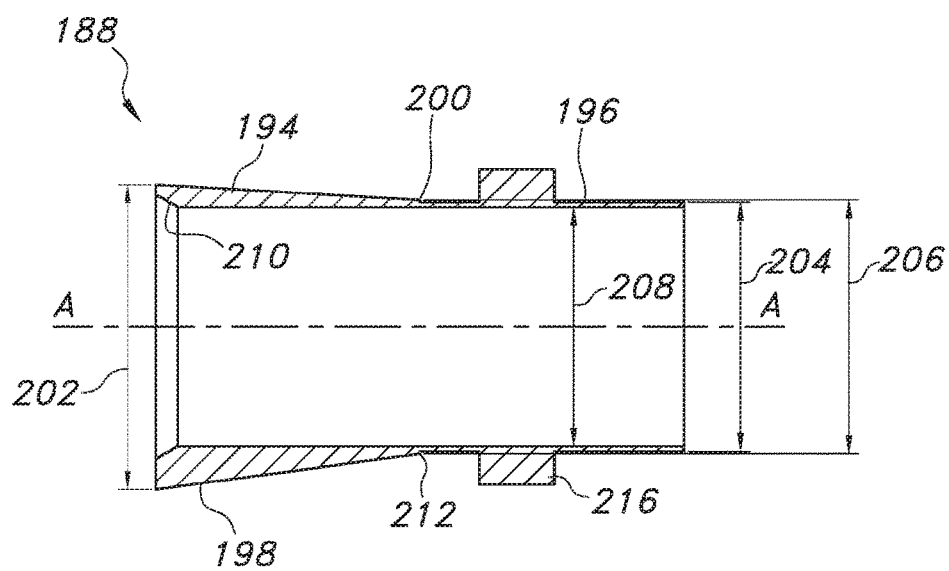
FIG. 7B

200
CUTTING HEAD FOR AN INTRAMEDULLARY REAMER

CROSS-REFERENCE TO RELATED APPLICATION

This application claims priority from U.S. Provisional Patent Application Ser. No. 62/374,896, filed Aug. 14, 2016.

FIELD OF THE INVENTION

The present invention relates to the art of orthopedic reamers, and more particularly, to cutting heads used for intramedullary reaming.

BACKGROUND

Reamers are tools used in orthopedic procedures to cut bone and associated tissue matter. Specifically, the cutting head of the present invention is designed to cut and bore into the intramedullary space or inner canal of a long bone such as a femur, tibia or humerus. Typically, the intramedullary space of a long bone is reamed to clean and create a space for an implant. As such, these reamers are required to be sterile and sharp. Using a dull reamer generates heat that typically leads to tissue necrosis and results in undesirable patient outcomes. A non-sterile reamer blade typically results in an infected and damaged intramedullary space that may lead to other problems for the patient.

Reamers are often used in trauma procedures. In one such procedure, a prosthetic implant is inserted into the intramedullary space to help mend a fractured bone. In the procedure, a flexible reamer is first inserted into the intramedullary space of the fractured bone. Using the intramedullary reamer, a cavity space is then formed for insertion of the implant into the fractured bone.

The preparation of the bone generally consists of removing the interior contents of the bone along its entire length so that a space is created allowing for insertion of the intramedullary nail. Removal of the interior contents occurs in steps where a cutting head having a relatively small cutting diameter is used to initiate a pilot hole and removal of the medullary contents. A series of cutting heads having progressively larger cutting diameters is then used to further increase the diameter of the intramedullary space and remove more bone and tissue material. The surgeon typically continues to use reamer cutting heads of increasing diameter until the appropriately sized space is created. After an appropriately sized space is created, an intramedullary nail is installed in the space to assist in healing of the traumatized bone.

However, prior art cutting heads have an inefficient blade design which tends to become increasingly dull, particularly when reaming large portions of bone material within a long bone, such as a femur. Furthermore, because of their high cost, traditional cutter heads are typically reused multiple times. Over time, as these reamer heads are used and reused, the cutting blades become dull. As a result, these less efficient prior art cutting heads tend to promote an increase in "head pressure" within the intramedullary canal. "Head pressure" is the pressure that forms ahead of the reaming bone cutter within the intramedullary canal. Increasing head pressure within the intramedullary canal may result in the occurrence of a "fat" embolism. A fat embolism occurs when fat becomes lodged within a blood vessel and obstructs blood flow. The occurrence of a fat embolism may result in a stroke or even death of the patient.

The intramedullary cutting head of the present invention, therefore, is designed to cut bone and tissue more efficiently than the cutting heads of the prior art. In contrast to the prior art, the cutting head blades are designed to reduce reactive torque and axial load while cutting, thus reducing trauma to the bone while cutting within the intramedullary space. In addition, the cutting head of the present invention is designed to efficiently remove cut material and debris so that the debris unobstructedly flows over the cutting head. Thus "head pressure" and the possibility of producing a fat embolism within the intramedullary canal is reduced.

Unfortunately, there is no simple way to evaluate cutting efficiency after these reamer tools have been used and reused. Many times it isn't until the surgeon has reused the reamer numerous times that he becomes aware that the reamer is cutting incorrectly. In many cases, an ineffective, dull, or contaminated reamer tool is not detected until well into the reaming procedure or even after the procedure is complete. Good surgical outcomes are largely dependent on the use of a sharp, sterile reamer that is in optimal condition. Poor surgical outcomes such as a damaged intramedullary space can occur as a result of using dull or contaminated reamers.

Accordingly, the present invention provides an embodiment of a cutting head having a novel blade and assembly design that improves cutting efficiency within the intramedullary space. The enhanced reaming efficiencies of the present invention decrease procedural times and minimize patient trauma. Furthermore, the intramedullary cutting head of the present invention ensures sharpness and cleanliness that promotes optimal patient outcomes.

SUMMARY OF THE INVENTION

The present invention provides various embodiments of a cutting head for use with an intramedullary reamer. The cutting head of the present invention is of a unitary body construction that comprises a cylindrically-shaped body having a convex shaped end wall. The cutting head comprises a bone cutting portion that extends to a barrel portion. The barrel portion, which is positioned proximal of the bone cutting portion, comprises a cavity therewithin that is configured to detachably connect the cutting head to a drive shaft.

The bone cutting portion comprises at least two cutting blades, each having a tissue cutting edge. The at least two cutting blades extend radially from the convex shaped end wall and in a proximal direction along the body. The plurality of at least two blades is positioned about the cutting head in an optimum separation distance between adjacent blades. This optimal separation distance allows for unobstructed removal of intramedullary debris over the cylindrical body. The various blades are arranged at a prescribed angular relationship that increases cutting efficiency and debris removal. The angled tissue cutting edge is oriented such that it follows an efficient helical path as it cuts through bone and tissue. In addition, each of the cutting blades comprises a transition blade segment positioned between the curved nose segment and a primary blade segment. The transition segment comprises a flat and a notch that is designed to minimize axial loading as the cutting head proceeds through the intramedullary canal during a surgical procedure. This optimal blade design further results in increased blade stability, cutting efficiency, and reduced head pressure.

The reamer cutting head of the present invention may comprise a shaft attachment interface. The shaft attachment interface, located at the proximal end of the cutting head, allows for a keyed attachment of the cutting head to the shaft. In an embodiment, the shaft attachment interface comprises a shaft having a projection that is received within a proximal end of the cutting head, such as the barrel portion, having a cutout portion with a cross-sectional geometrical shape that corresponds to the shape of the shaft projection. The shaft projection is received and mated with the cutout portion of the cutting head in a keyed relationship. The shaft attachment interface can be provided with a removable interference fit, a locking junction, a dovetail junction or it can be designed as an integral portion of the cutting head and shaft assembly.

Furthermore, a protective sleeve may be removably attached to the proximal end of the reamer cutting head. The sleeve provides an alternative means in which to secure the drive shaft to the cutting head. In addition, the sleeve provides a protective covering that minimizes potential disengagement of the shaft from the cutting head. In an embodiment, the sleeve comprises a tapered distal end collar that surrounds the drive shaft and attaches to the cutting head proximal end.

The cutting head of the present invention may be manufactured by a metal injection mold process. In this process, the reamer cutting head is fabricated by injecting a composite mixture comprising a powdered metal and a binder. The metal injection mold process forms the cutting head having a unitary body construction. Metal injection molding provides a low-cost production process that reduces manufacturing time. In addition, the metal injection molding process avoids the need for expensive grinding operations and assembly of individual blade component pieces.

BRIEF DESCRIPTION OF THE DRAWINGS

FIG. 7 illustrates an embodiment of a sleeve that may be attached to either of the cutting heads shown in FIG. 1.

FIG. 7A shows a top view of the embodiment of the sleeve shown in FIG. 7.

FIG. 7B is a cross-sectional view of the embodiment of the sleeve shown in FIG. 7 taken along longitudinal axis A-A.

DETAILED DESCRIPTION OF THE PREFERRED EMBODIMENTS

Figure 1:
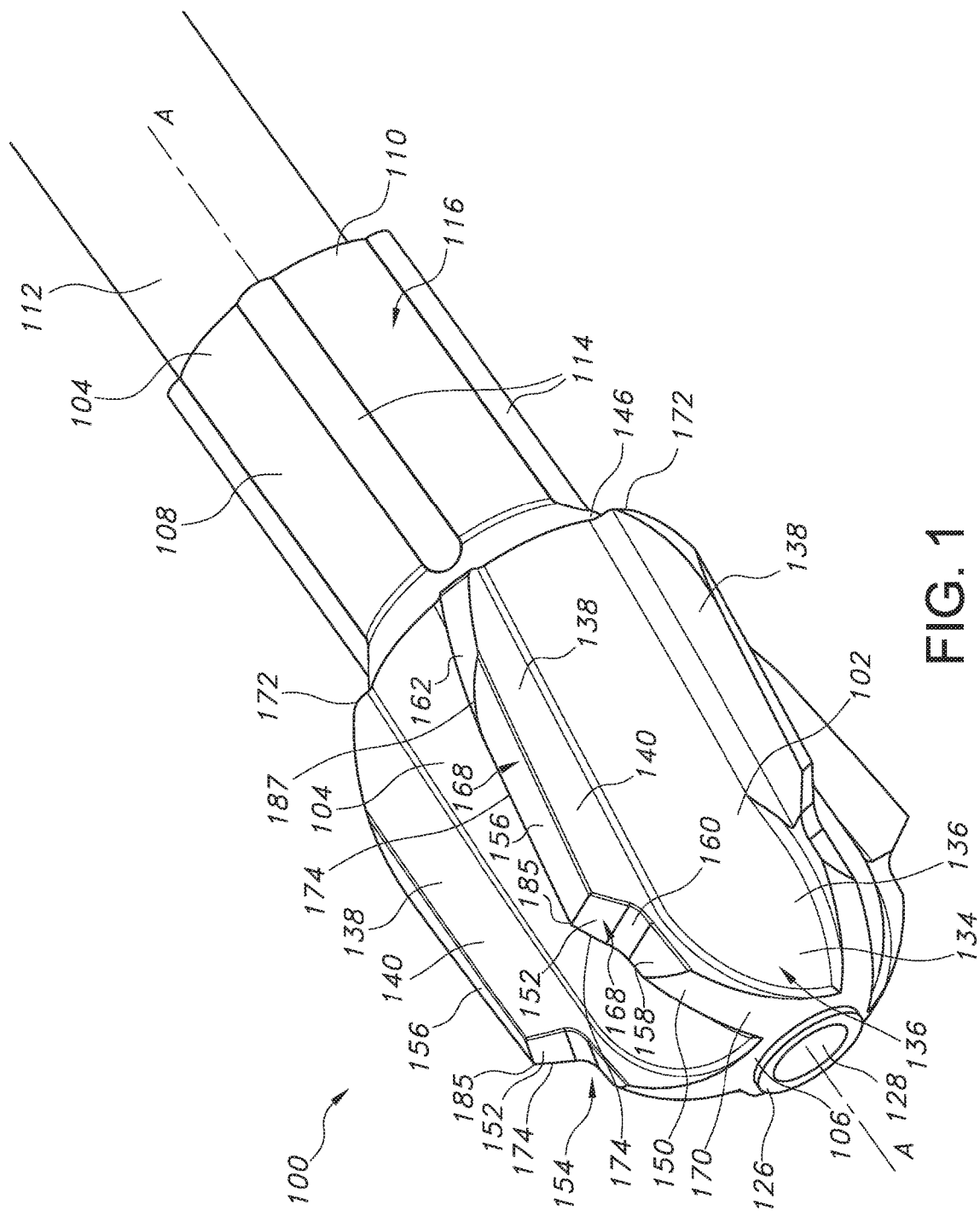
FIG. 1 is a perspective view of an embodiment of the cutting head of the present invention.
Figure 2:
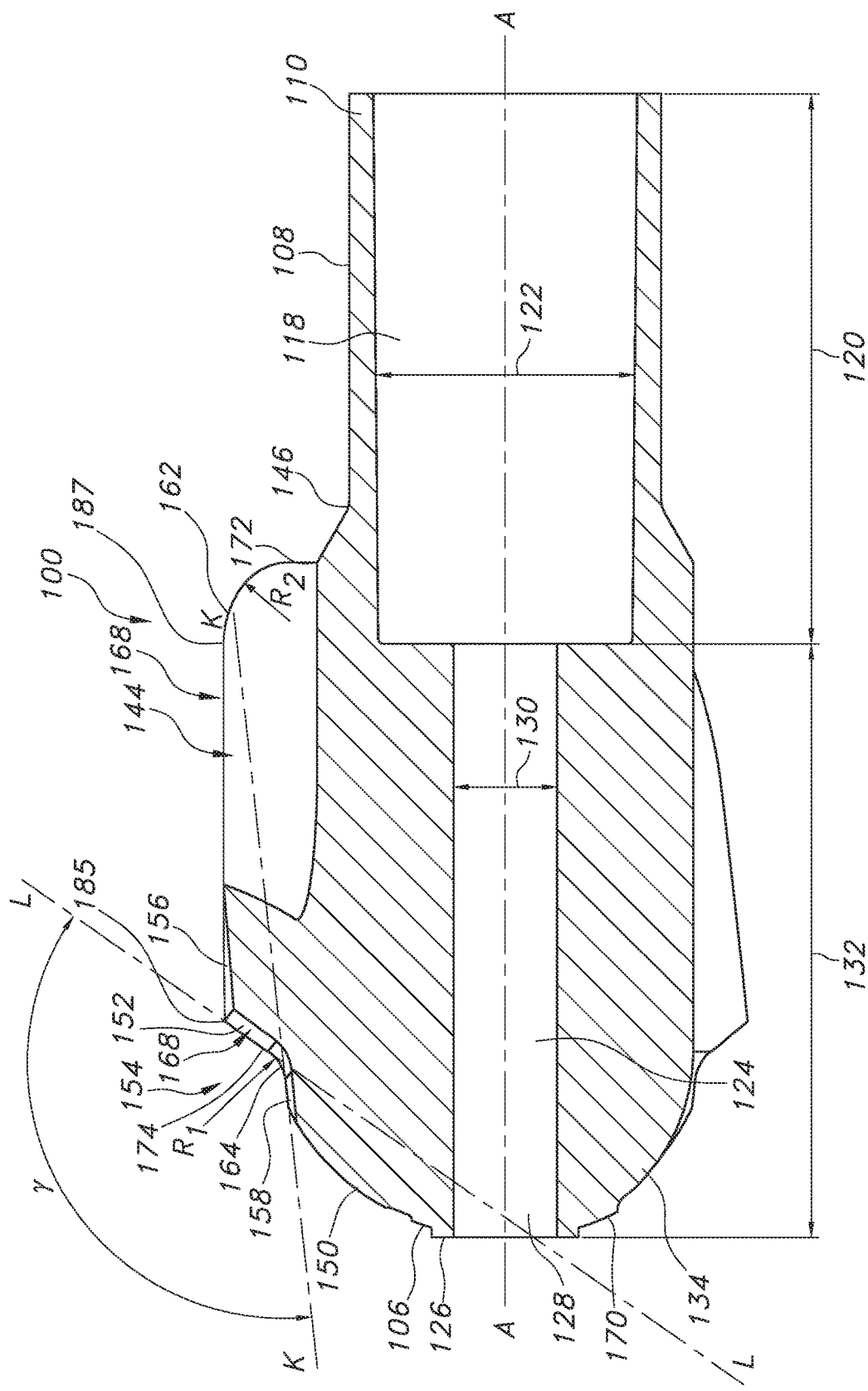
FIG. 2 shows a cross-sectional view of the cutting head shown in FIG. 1.
Figure 3:
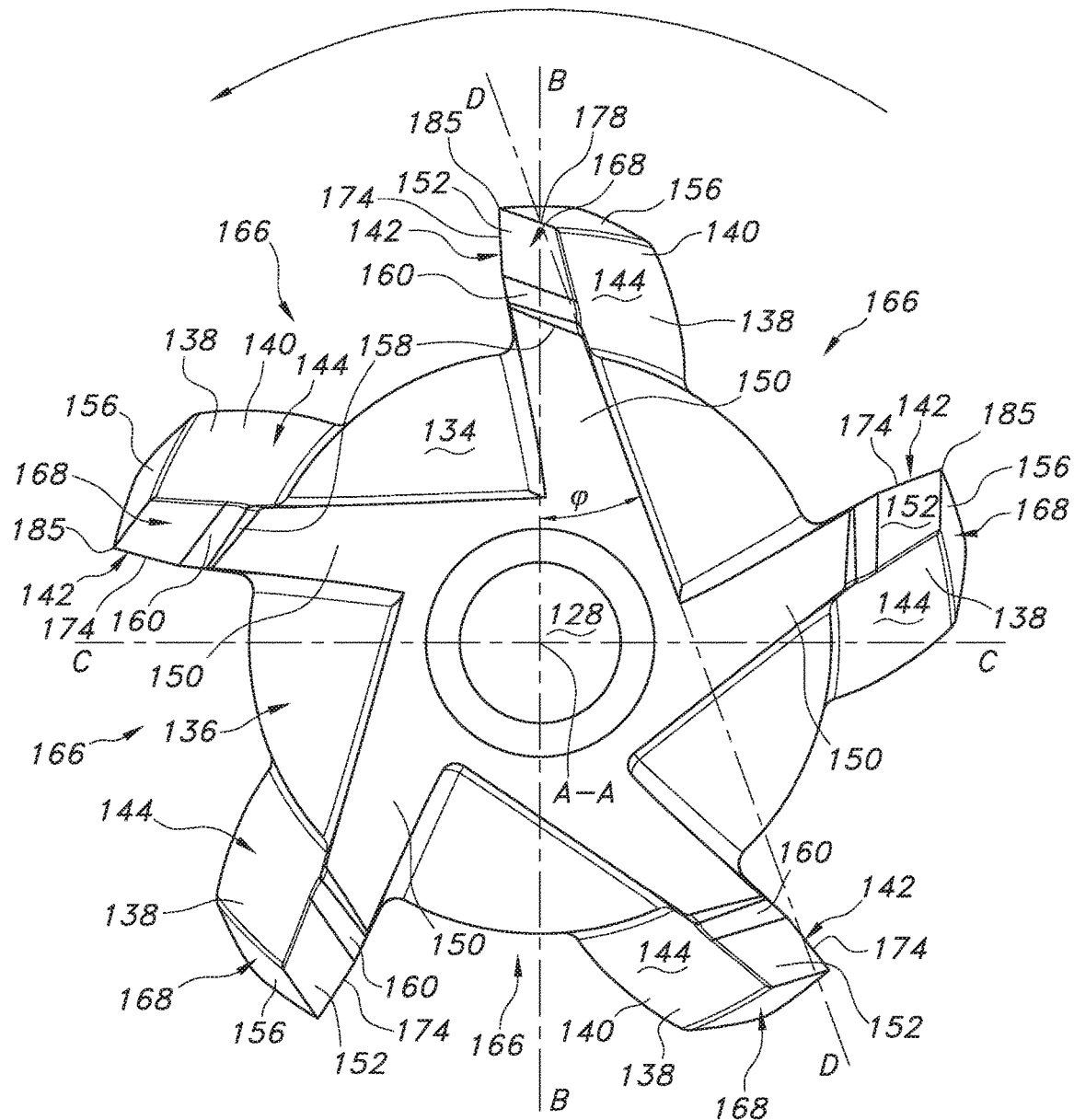
FIG. 3 illustrates a front view taken from the distal end of the embodiment of the cutting head shown in FIG. 1.
Figure 4:
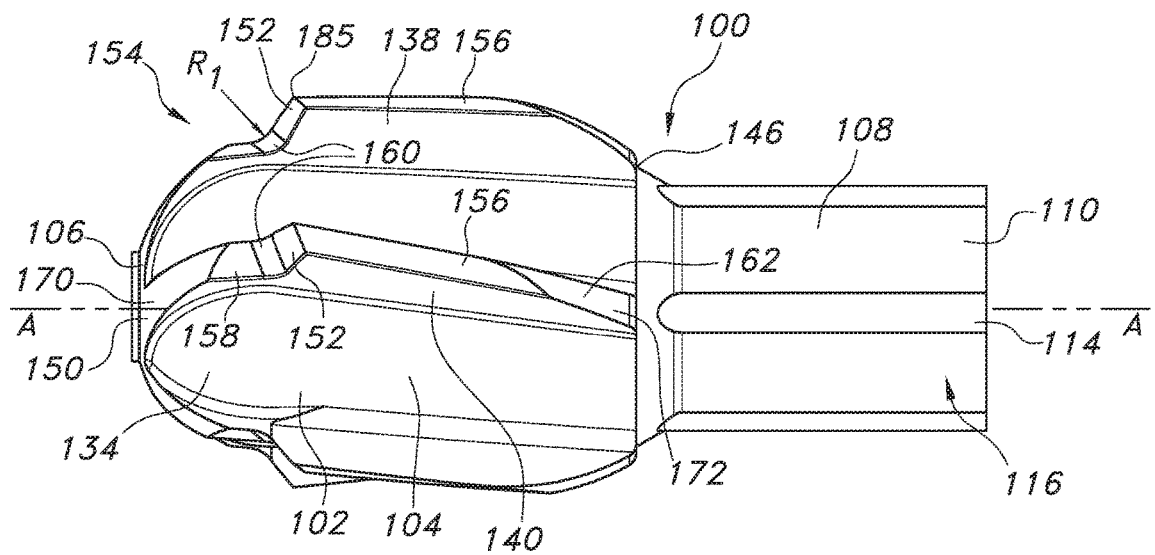
FIG. 4 illustrates a side view of the embodiment of the cutting head shown in FIG. 1.

Now turning to the figures, FIGS. 1-5, 8 and 9 illustrate an embodiment of a cutting head 100 that is configured to cut and remove bone and tissue from the intramedullary canal. As shown in FIG. 1, the cutting head 100 comprises a cylindrically shaped body 102 that extends along longitudinal axis A-A from a distal bone cutting portion 104 having a distal end 106 to a proximal barrel portion 108 having a proximal end 110. The bone cutting portion 104 provides for cutting and removal of bone and tissue from the intramedullary canal during a surgical procedure. The barrel portion 108 provides for a detachable connection of the cutting head 100 to a drive shaft 112 (FIG. 1). For example, a drive shaft 26 connected to a rotary motor (not shown). In an embodiment, a plurality of spaced apart ribs 114 extend outwardly from an exterior barrel surface 116. As shown in FIGS. 1 and 4, the ribs 114 extend axially and are spaced from, but parallel to the longitudinal axis A-A. The plurality of ribs 114 provides lateral stability to the cutting head 100 as it bores through the intramedullary canal.

In an embodiment, a proximal cavity 118 (FIG. 2) is dimensioned to receive a drive shaft 112. The cavity 118 extends along the longitudinal axis A-A through the bone cutting head proximal end 110 and at least partially within the barrel portion 108. In an embodiment, the cavity 118 is dimensioned to provide an interference fit with the drive shaft 112. In a preferred embodiment, the cavity 118 has a length 120 that ranges from about 0.5 cm to about 2 cm and a diameter 132 that ranges from about 0.5 cm to about 1 cm.

In an embodiment, a lumen 124 in open communication with cavity 118 extends along the longitudinal axis A-A through the bone cutting portion 104. As illustrated in FIG. 2, the lumen 124 extends through the cutting head distal end 106 creating a distal opening 128 therethrough. The lumen 124 provides a channel for the removal of the cut bone and tissue from the intramedullary canal during a surgical procedure. In addition, the lumen 124 provides an opening for a guidewire (not shown) to extend therethrough. The guidewire may be used to help control the movement and positioning of the cutting head 100 within the intramedullary canal. In a preferred embodiment, the lumen 124 has a diameter 130 that ranges from about 0.1 cm to about 0.5 cm and a length 132 that ranges from about 0.5 cm to about 2 cm.

In an embodiment, the body 102 comprises a nose portion 134 having a planar end wall 126 at the cutting head distal end 106. In an embodiment, the nose end wall 126 may have an exterior surface 136 that is curved. As illustrated in FIGS. 1, 2, 4, and 5, the nose portion 134 has a bulbous construction in which the exterior distal surface 136 is of a convex shape that curves outwardly and proximally from the end wall 126.

At least two spaced apart cutting blades 138 extend outwardly from the exterior surface of the body 102. In an embodiment, as shown in FIGS. 1 and 3, the cutting blades 138 extend in a proximal direction from the nose distal end wall 126 towards the cutting head proximal end 110. As illustrated in FIG. 3, five spaced apart cutting blades 138 are shown. However, the cutting head 100 may be designed with at least two spaced apart cutting blades 138.

As illustrated, each of the cutting blades 138 comprises a blade sidewall 140 having opposed leading and trailing sidewall surfaces 142, 144 that outwardly extend from the exterior surface of the body 102. A relief surface 168 resides between the opposed leading and trailing sidewall surfaces 142, 144 and extends from the nose distal end wall 126 to a cutting portion proximal end 146 adjacent to where the cutting portion 104 meets the barrel portion 108. In an embodiment, the opposing leading and trailing sidewall surfaces 142, 144 define a blade width 148 (FIG. 5B)

therebetween. In an embodiment, the blade width 148 may range from about 0.1 cm to about 1 cm.

As illustrated in FIGS. 1-5, each cutting blade 138 comprises a nose blade segment 150 that resides at the cutting head distal end 106 and immediately adjacent to the planar end wall 126. The nose blade segment 150 extends in a proximal direction toward a primary blade segment 152. A blade transition segment 154, comprising a flat 158 and a notch 160, resides between the nose blade segment 150 and the primary blade segment 152. A proximal blade segment 156 extends in a proximal direction from the primary blade segment 152 to a trailing blade segment 162 that resides at the bone cutting portion proximal end 146.

In an embodiment, the curved structure of the nose blade segment 150 helps center the cutting head 100 within the intramedullary canal and direct tissue and bone to the primary and proximal blade segments 152, 156 where they are cut. The blade transition segment 154 comprising the flat 158 and notch 160 transitions the blade from the curved nose segment 150 to the primary blade segment 152 and serves to help direct tissue and bone to the primary and proximal blade segments 152, 156, respectively. Furthermore, the transition segment 154 helps to minimize mechanical stress and the axial load that is applied to the cutting head 100 while in use during a surgical procedure. Experimental testing has revealed that the transition segment 154 reduces the axial load by as much as 50 percent in comparison to a cutting head that does not comprise the transition segment 154.

As illustrated in FIGS. 1-6, the blade transition segment 154 resides between the nose blade segment 150 and the primary blade segment 152. As shown, the flat 158 extends in a proximal direction from the nose blade segment 150 and meets the notch 160. The notch 160 extends from the flat 158 and meets the primary blade segment 152. In an embodiment, as shown in FIGS. 1 and 3-6, the notch 160 has a width that extends between the leading and trailing sidewall surfaces 142, 144. In addition, the notch 160 has a curved surface 164 that is at least partially recessed within the relief surface 168. In an embodiment, the curved notch 160 is concave having a radius of curvature $R_1$ (FIGS. 2 and 4) that ranges from about 0.1 cm to about 0.5 cm.

In an embodiment, each of the cutting blades 138 is oriented so that the leading surface 142 of one cutting blade 138 faces the trailing surface 144 of an adjacent cutting blade 138. A gap 166, forming a clearance space, resides between two adjacently positioned cutting blades 138. In an embodiment, the gap 166 resides between the leading and trailing blade sidewall surfaces 142, 144 that are positioned immediately adjacent to each other. In an embodiment, the gap 166 is dimensioned to provide space between adjacent cutting blades 138 for the removal of cut bone and tissue during a surgical procedure.

In an embodiment, the blade relief surface 168 extends in a proximal direction from the nose distal end wall 126 to a cutting blade proximal end 172 located at the bone cutting portion proximal end 146. A tissue cutting edge 174 is formed at the intersection of the leading sidewall and relief surfaces 142, 168. In an embodiment, the tissue cutting edge 174 is at least partially formed along a length of the cutting blade 138 from the nose distal end wall 126 to the cutting blade proximal end 172. In a preferred embodiment, the tissue cutting edge 174 extends along the flat 158, the notch 160, the primary blade segment 152, and the proximal blade segment 156.

In an embodiment, the cutting head 100 is rotated about the longitudinal axis A-A in either a clockwise or counter-clockwise direction. In a preferred embodiment, the cutting head 100 is rotated in a clockwise direction so that the tissue cutting edge 174 leads the trailing sidewall surface as the cutting head 100 is rotated within the intramedullary canal. It is noted that the rotational arrows shown in FIGS. 3, 5A, 5B and 5C, indicate the preferred rotational direction.

In an embodiment, that portion of the relief surface 168 along the nose blade segment 150 is curved. As illustrated in FIGS. 1 and 4-8, that portion of the relief surface 168 that extends along the nose blade segment 150 has a curvature that is conformal to the exterior nose surface 136. In an embodiment, a portion of the relief surface 168 that radiates from the nose end wall 126 at the opening 128 is about flush with the exterior nose surface 136. In an embodiment, the blade sidewall 140 has a height 176 (FIG. 5B) that outwardly extends from the exterior surface of the body 102. In an embodiment, the blade sidewall height 176 gradually increases from the cutting head distal end 106 to the flat 158. In an embodiment, the blade height 176 where the nose segment 150 meets the flat 158 ranges from about 0.1 cm to about 0.5 cm. Furthermore, the edges of the blade relief surface 168 along the nose segment 150 where the leading and trailing surfaces 142, 144 is beveled. The beveled edges of the relief surface 168 and inclined blade construction along the nose segment 150 are intended to help guide the cutting head 100 through the intramedullary canal. In addition, the curved construction of the nose segment 150 is designed to direct tissue and bone towards the primary and proximal blade segments with a reduced mechanical axial load applied to the cutting head 100 during a surgical procedure. Furthermore, the relief surface 168 along the nose blade segment 150, the primary blade segment 152, and the proximal blade segment 156 is designed with a ramp surface such that the height of the leading sidewall 142 is greater than the height of the trailing sidewall 144.

FIG. 2 is a cross-sectional view of the cutting head 100. This figure further illustrates the curvature of the edge formed at the intersection of the trailing sidewall 144 and the relief surface 168 of the cutting blade 138 as the trailing sidewall extends in a proximal direction towards the cutting head proximal end 110. As illustrated, the edge along the intersection of the trailing sidewall 144 and relief surface 168 curves towards the exterior surface of the body 102 as the cutting blade 138 extends in a proximal direction. In an embodiment, the edge formed at the intersection of the trailing sidewall 144 and relief surface 168 along the proximal blade segment 156 extends about parallel to the longitudinal axis A-A. As illustrated, the edge from point 185 where the primary blade segment 152 and the proximal blade segment 156 meet, to point 187 where the proximal blade segment 156 meets the trailing blade segment 162 is about parallel to the longitudinal axis A-A.

As shown, at point 187 where the proximal blade segment 156 meets the trailing blade segment 162, the relief surface 168 curves from the leading sidewall 142 to the trailing sidewall 144 and towards the cylindrically-shaped body 102. In an embodiment, the edge at the intersection of the trailing sidewall 144 and relief surface 168 from the point 187, where the proximal blade segment 156 meets the trailing blade segment 162 to the proximal end 172 has a radius of curvature $R_2$ that ranges from 0.1 mm to about 1.0 mm. In a preferred embodiment, the radius of curvature $R_2$ is about 0.5 mm.

FIG. 3 illustrates an end view of the cutting head 100 taken from the cutting head distal end 106. In the embodiment, the trailing blade sidewall surface 144 along the nose segment 150 is orientated at a nose blade tilt angle φ that extends between imaginary lines B-B and D-D. Imaginary line B-B extends perpendicular to the longitudinal axis A-A and through a point 178 that bisects the width of the primary blade segment 152 extending between the opposing leading and trailing blade sidewall surfaces 142, 144. Imaginary line D-D is coincident with the trailing blade sidewall surface 144 along the nose segment 150 and intersects line B-B at the midpoint 178. In a preferred embodiment, the nose blade tilt angle φ may range from about 10° to about 50°. The nose blade tilt angle encourages efficient rotation of the cutting head 100 in the intramedullary canal as well as establish a cutting blade helical cutting path.

Figure 5:
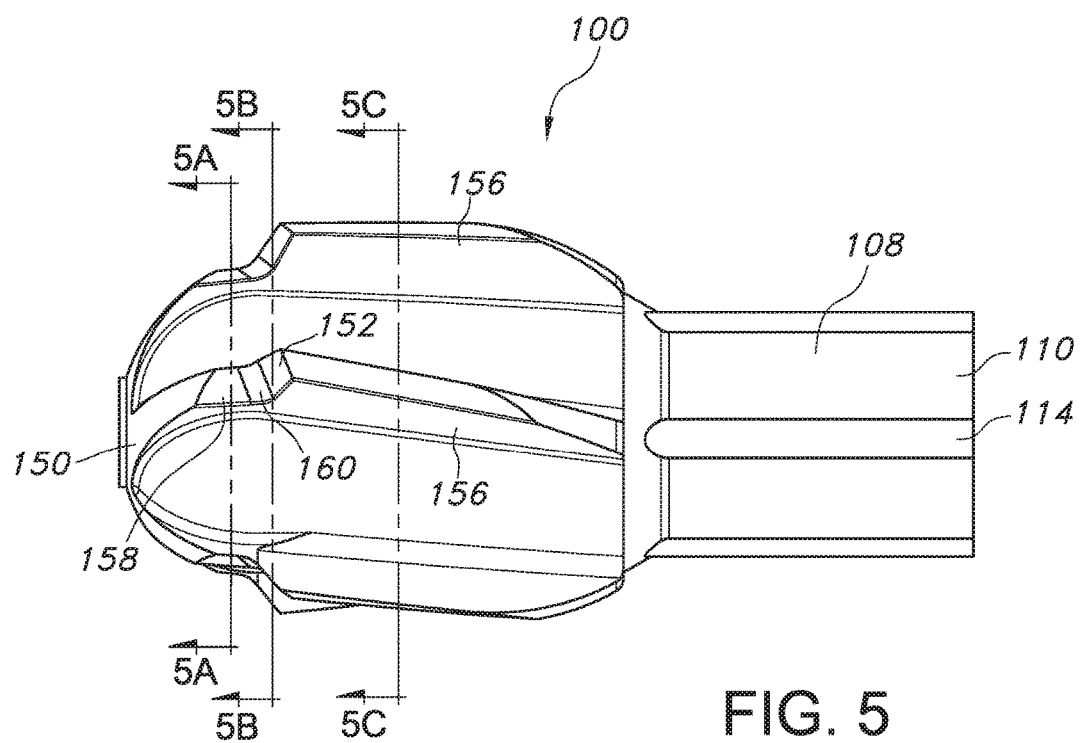
FIG. 5 illustrates a side view of the cutting head shown in FIG. 1 illustrating the location of the cross-sectional views shown in FIGS. 5A-5C.
Figure 5A:
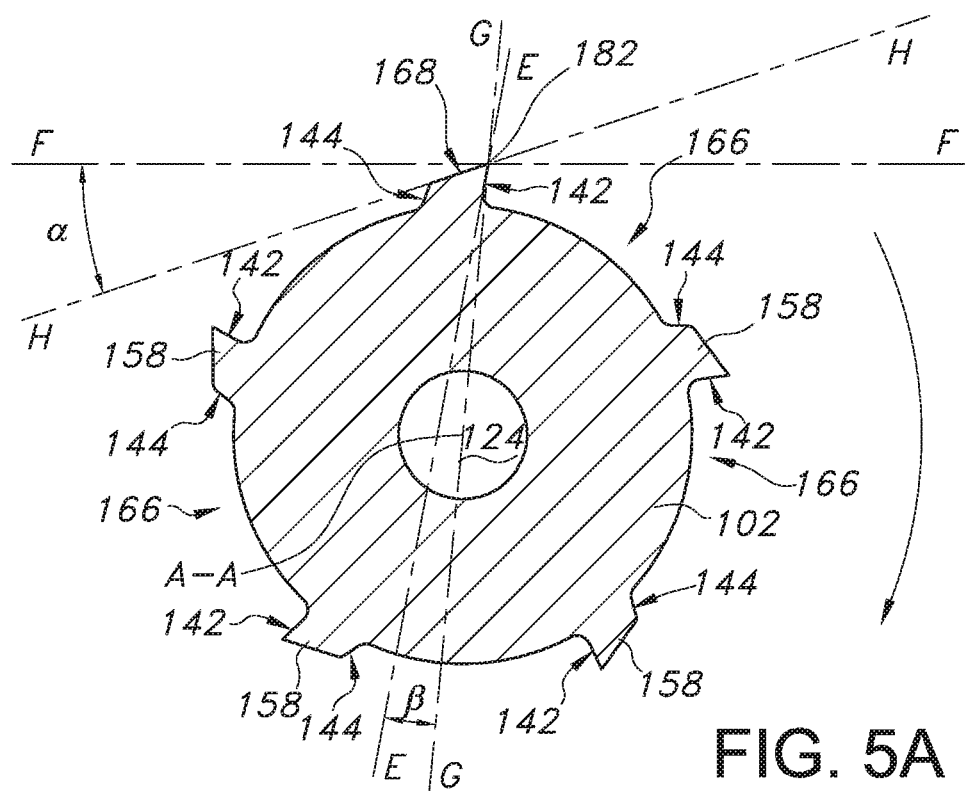
FIG. 5A is a cross-sectional view taken along sectional line 5A-5A shown in FIG. 5.
Figure 5B:
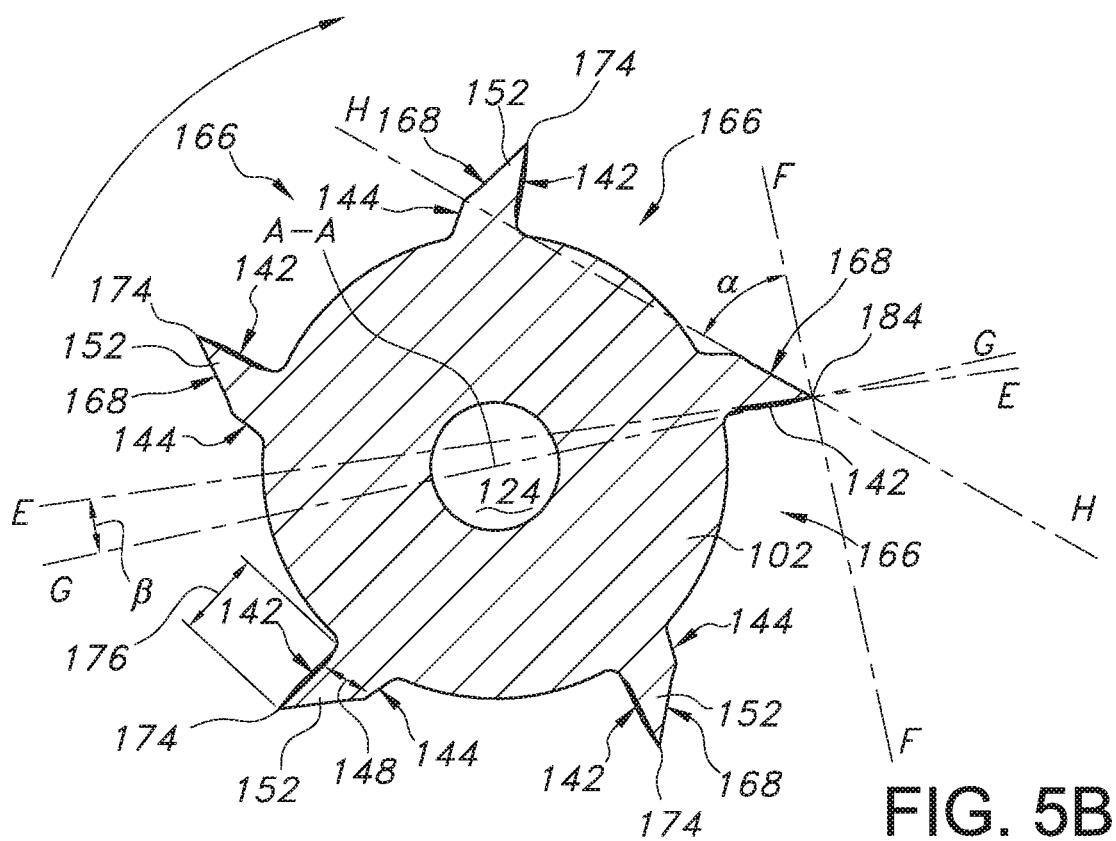
FIG. 5B is a cross-sectional view taken along sectional line 5B-5B shown in FIG. 5.
Figure 5C:
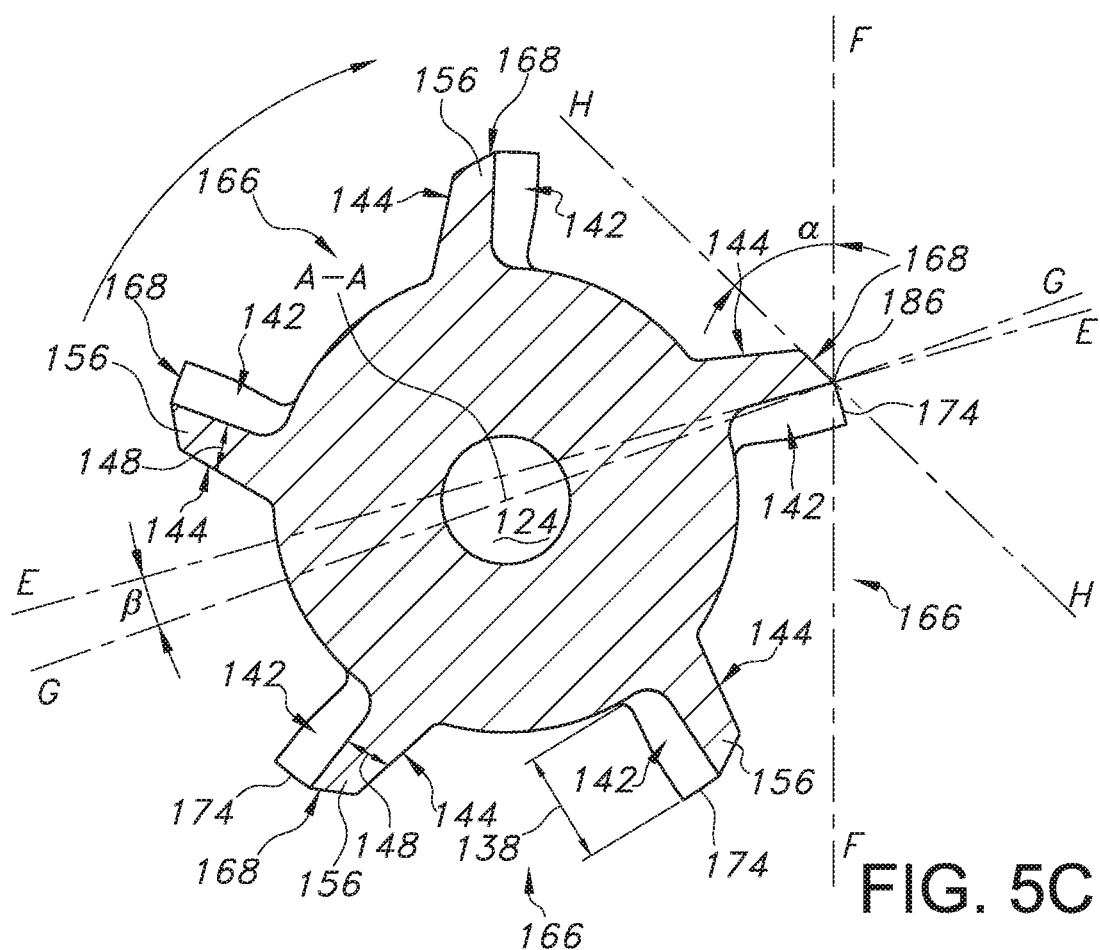
FIG. 5C is a cross-sectional view taken along sectional line 5C-5C shown in FIG. 5.

FIGS. 5A, 5B, and 5C illustrate cross-sectional views of the cutting head 100 taken perpendicularly at different locations along longitudinal axis A-A shown in FIG. 5. FIG. 5A illustrates a cross-sectional view taken along the flat 158. FIG. 5B illustrates a cross-sectional view taken along the primary blade segment 152 and FIG. 5C illustrates a cross-sectional view taken along the proximal blade segment 156. In an embodiment, for each cutting blade 138, there is an infinite number of cross-sections from the end wall surface 136 to the cutting portion proximal end 146, FIGS. 5A-5C being just a few of them. As shown in the cross-sections of FIGS. 5A-5C, a blade relief angle α extends between imaginary line F-F and imaginary line H-H and a blade rake angle β extends between imaginary line E-E and imaginary line G-G.

FIG. 5A illustrates a cross-sectional view oriented perpendicular to the longitudinal axis A-A intersecting the flat 158. As shown, the blade rake angle β along the flat 158 extends between imaginary lines E-E and G-G. Imaginary line E-E is coincident to the leading sidewall surface 142 and extends through a point 182 that resides at the intersection of the relief surface 168 and the leading sidewall surface 142 at this section. It is noted that in the embodiment shown in the cross-sectional view of FIG. 5A, the intersection point 182 is the outermost endpoint of the tissue cutting edge 174 at this section. Imaginary line G-G extends through longitudinal axis A-A and point 182 where the relief and leading surfaces 168, 142 meet. In an embodiment, the relief angle α extends between imaginary lines F-F and H-H. As illustrated, imaginary line F-F is positioned perpendicular to imaginary line G-G and extends through the point 182. Imaginary line H-H is coincident with that portion of the relief surface 168 that resides along the flat 158. In an embodiment, the cutting blade 138 may be constructed so that the rake angle β along the flat 158 may range from about 2° to about 8°. More preferably, the rake angle β along the flat 158 may be about 6° to about 8°. The cutting blade 138 may be constructed so that the relief angle α along the flat 158 may range from about 15° to about 35°. In a preferred embodiment, the blade relief angle α along the flat 158 may range from about 25° to about 35°.

As previously mentioned, the primary blade segment 152 provides a cutting surface designed to ream bone and tissue within the intramedullary canal. As shown, in FIGS. 2 and 4, the primary blade segment 152 extends in an outwardly direction from the notch 160 of the transition blade segment 154. As illustrated, the sidewall 140 along the primary blade segment 152 has a height 176 that is greater than the sidewall 140 along the flat and notch segments 158, 160. In an embodiment, the height of the sidewall 140 along the primary blade segment 152 may range from about 0.3 cm to about 1 cm.

In addition, as illustrated in FIGS. 1, 2, and 4-5, that portion of the relief surface 168 along the primary blade segment 152 is a ramped surface that extends outwardly and proximally from the notch 160. As particularly shown in FIG. 2, that portion of the relief surface 168 along the primary blade segment 152 is oriented at a primary blade segment angle γ that extends between imaginary lines K-K and L-L. As illustrated, imaginary line K-K is coincident with the intersection of the leading sidewall surface 142 and that portion of the relief surface 168 along the flat 158. Imaginary line L-L is coincident with the tissue cutting edge 174 at the intersection of the leading sidewall surface 142 (FIG. 3) and that portion of the relief surface 168 along the primary blade segment 152. In an embodiment, the primary blade segment angle γ is an obtuse angle. In a preferred embodiment, the primary blade segment angle γ may range from about 100° to about 160° as the incline of the ramped relief surface 168 along the primary blade segment 152 is modified.

FIG. 5B illustrates a cross-sectional view oriented perpendicular to the longitudinal axis A-A intersecting the primary blade segment 152 (FIG. 1). As shown, the blade rake angle β along the primary blade segment 152 extends between imaginary lines E-E and G-G. In an embodiment, imaginary line E-E is coincident to the leading sidewall surface 142 and extends through a point 184 that resides at the intersection of the relief surface 168 and the leading sidewall surface 142 along the primary blade segment 152. It is noted that in the embodiment shown in the cross-sectional view of FIG. 5B, the intersection point 184 is the outermost endpoint of the tissue cutting edge. Imaginary line G-G extends through longitudinal axis A-A and point 184 at which the relief and leading surfaces 168, 142 meet. In an embodiment, the relief angle α extends between imaginary lines F-F and H-H. As illustrated, imaginary line F-F is positioned perpendicular to imaginary line G-G and extends through the point 184. Imaginary line H-H is coincident to the relief surface 168 along the primary blade segment 152. In an embodiment, the cutting blade 138 may be constructed so that the blade rake angle β along the primary blade segment 152 may range from about 2° to about 6°. In a preferred embodiment, the blade rake angle β along the primary blade segment 152 is from about 4° to about 6°. The cutting blade 138 may be constructed so that the relief angle α along the primary blade segment 152 may range from about 25° to about 35°. In a preferred embodiment, the blade relief angle α along the primary blade segment 152 is from about 30° to about 32°.

As illustrated in FIGS. 1, and 3-8, the proximal blade segment 156 provides a cutting surface designed to cut bone and tissue within the intramedullary canal. In an embodiment, the height 176 of the sidewall 140 along the proximal blade segment 156 determines the diameter of the opening formed within the intramedullary canal by the cutting head 100 of the present invention. In an embodiment, the diameter within the opening formed within the intramedullary canal is defined by the height of the sidewall 140 at point 185 (FIG. 1), which is at the intersection of the leading and relief surfaces 142, 168 where the primary and proximal blade segments 152, 156 meet. In addition, the height 176 of the sidewall 140 along the proximal blades segment 156 may be constant. In an embodiment, the height 176 of the sidewall 140 along the proximal blade segment 156 may be about the same as the height of the sidewall 140 of the primary blade segment 150 at point 185. In an embodiment, the height 176 of the sidewall 140 along the proximal blade segment 156 may range from about 0.3 cm to about 1 cm.

FIG. 5C illustrates a cross-sectional view oriented perpendicular to the longitudinal axis A-A along the proximal blade segment 156. As shown, the blade rake angle β along the proximal blade segment 156 extends between imaginary lines E-E and G-G. In an embodiment, imaginary line E-E is coincident with the leading sidewall surface 142 and extends through a point 186 that resides at the intersection of that portion of the relief surface 168 in the proximal blade segment 156 and the leading sidewall surface 142. It is noted that in the embodiment shown in the cross-sectional view of FIG. 5C, the intersection point 186 is the outermost endpoint of the tissue cutting edge. Imaginary line G-G extends through longitudinal axis A-A and point 186 at which the relief and leading surfaces 168, 142 meet. In an embodiment, the relief angle α extends between imaginary lines F-F and H-H. As illustrated, imaginary line F-F is positioned perpendicular to imaginary line G-G and extends through the point 186. Imaginary line H-H is coincident with the relief surface 168 along the proximal blade segment 156. In an embodiment, the cutting blade 138 may be constructed so that the blade rake angle β along the proximal blade segment 156 may range from about 2° to about 6°. In a preferred embodiment, the blade rake angle β along the proximal blade segment 156 is from about 2° to about 4°. In an embodiment, the cutting blade 138 may be constructed so that blade relief angle α along the proximal blade segment 156 ranges from about 23° to about 35°. The orientation of the relief angle α helps to efficiently cut bone and tissue from within the intramedullary canal, thus reducing reactive torque and axial loading.

In an embodiment, that portion of the relief surface 168 residing in the trailing blade segment 162 is curved towards the cylindrically-shaped body 102. Unlike the primary and proximal blade segments 152, 156 the trailing blade segment 162 is not intended to cut tissue or bone. As illustrated, this portion of the trailing blade relief surface 168 is constructed such that it curves downward in a proximal direction from the proximal blade segment 156 to the cylindrically-shaped cutting head body 102 and away from the tissue cutting edge 174 of the primary and proximal blade segments 152, 156. In an embodiment, the trailing blade segment 162 helps to stabilize the cutting blade 138 of the cutting head 100 as it reams within the intramedullary canal.

Figure 6:
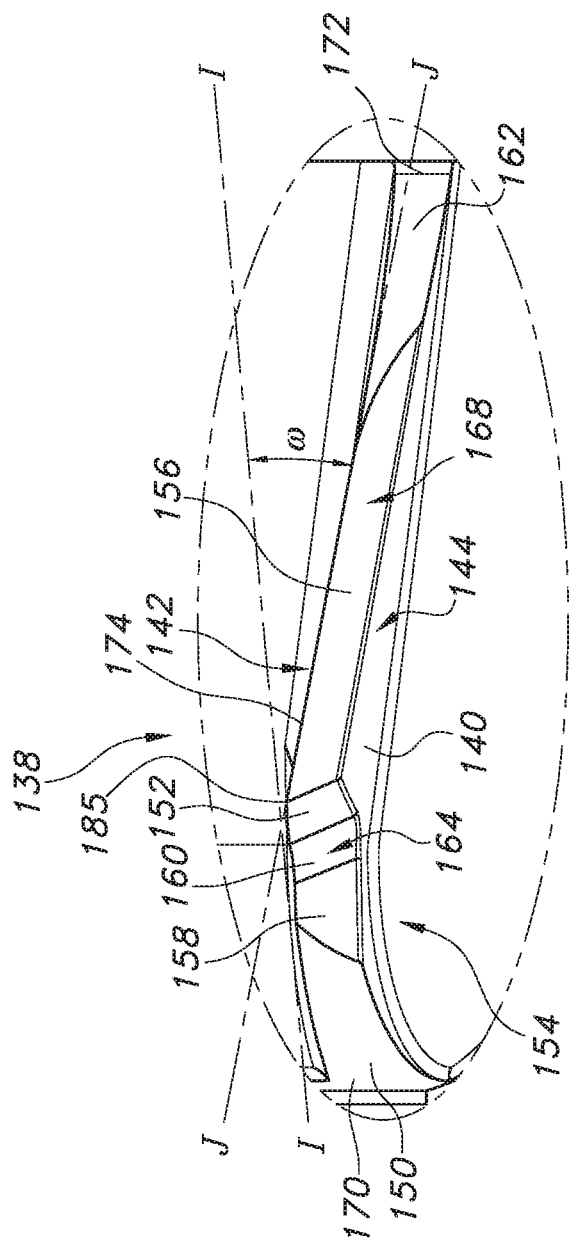
FIG. 6 illustrates a magnified view of an embodiment of a cutting blade of the cutting head shown in FIG. 1.

FIG. 6 illustrates a magnified perspective view of an embodiment of the cutting blade 138 of the cutting head 100 of the present invention. As shown, the proximal blade segment 156 is constructed such that it deflects from the nose blade segment 150 at a deflection angle ω. This deflection angle ω provides for the cutting blade 138 to cut in a helical path, thus reducing reactive torque and axial load during a surgical procedure. As illustrated in FIG. 6, the proximal blade segment deflection angle ω is defined as the angle between imaginary line I-I and imaginary line J-J. Imaginary line I-I is coincident with the intersection of the leading sidewall surface 142 and that portion of the relief surface 168 residing along the nose blade segment 150, and imaginary line J-J is coincident with the intersection of the leading sidewall surface 142 and this portion of the relief surface 168 along the proximal blade segment 156. In an embodiment, the deflection angle ω may range from about 5° to about 15°.

FIGS. 7, 7A, and 7B illustrate an embodiment of an optional sleeve 188 that may be removably attached to the cutting head proximal end 110. As shown, the sleeve 188 comprises spaced apart distal and proximal sleeve ends 190, 192. In an embodiment, the sleeve 188 forms a transition between the barrel portion 108 and an attached drive shaft 112. The sleeve 188 is constructed to provide an improved seal between the drive shaft 112 and the cutting head 100. Furthermore, the sleeve 188 is designed to minimize the possibility that the junction between the cutting head 100 and the drive shaft 112 at the barrel proximal end may obstruct the insertion or removal of the cutting head 100 within the intramedullary canal.

In an embodiment, the sleeve 188 comprises a collar 194 that extends to a tube portion 196. The collar 194 having spaced apart collar distal and proximal ends 198, 200, resides at the sleeve distal end 190 such that the collar distal end 198 forms the distal end of the sleeve 188. The collar 194 has a tapered construction comprising a distal end outer diameter 202 that is greater than a proximal end outer diameter 204. As shown, the tube portion 196 comprising a tube outer diameter 206 and a tube inner diameter 208, extends along longitudinal axis A-A from the collar proximal end 200. The collar distal end 198 is dimensioned to receive the barrel proximal end. In an embodiment, the collar 194 may comprise a chamfer 210 that is formed within the collar interior at the collar distal end 198. In an embodiment, the chamfer 210 extends annularly about the interior of the collar distal end 198. In an embodiment, the chamfer 210 forms a surface that physically contacts the proximal end of the cutting head barrel portion 108. An adhesive positioned along the chamfer surface may be used to connect the barrel portion 108 of the cutting head 100 to the sleeve 188.

In an embodiment, the proximal collar end outer diameter 204 is greater than the tube portion outer diameter 206. This preferred relationship between the two diameters of the collar and tube portions allows for an annular ledge 212 to be formed at the proximal collar end 200. In addition, a plurality of spaced apart collar ribs 214 may extend longitudinally along the exterior collar surface. These collar ribs 214 are dimensioned similarly to the exterior ribs that extend along the barrel portion exterior surface. In an embodiment, a ring 216, such as a ring of shrink wrap or other compression material, may be positioned around the tube outer diameter 206. As such, the ring 216 is designed to constrict the tube portion 196 around the drive shaft 112 positioned within the tube 196, thereby forming an interference fit therebetween.

Figure 8:
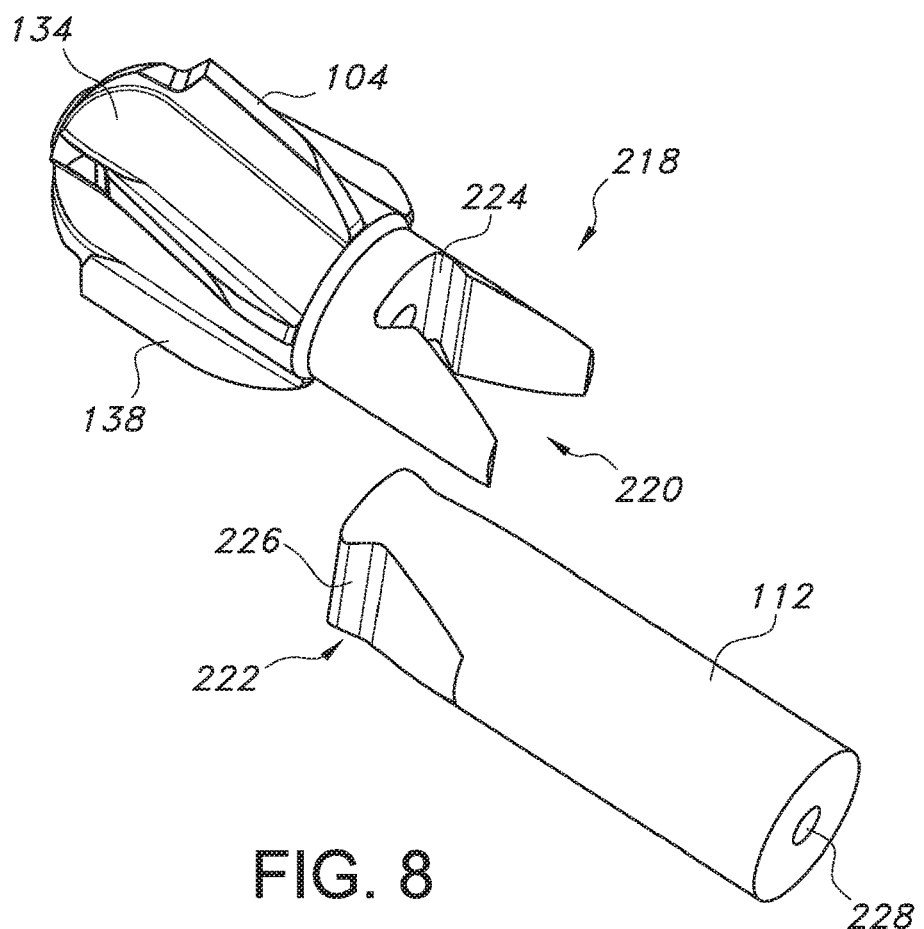
FIGS. 8 and 9 illustrate an embodiment of a shaft attachment interface that may be used to attach the cutting head shown in FIG. 1.
Figure 9:
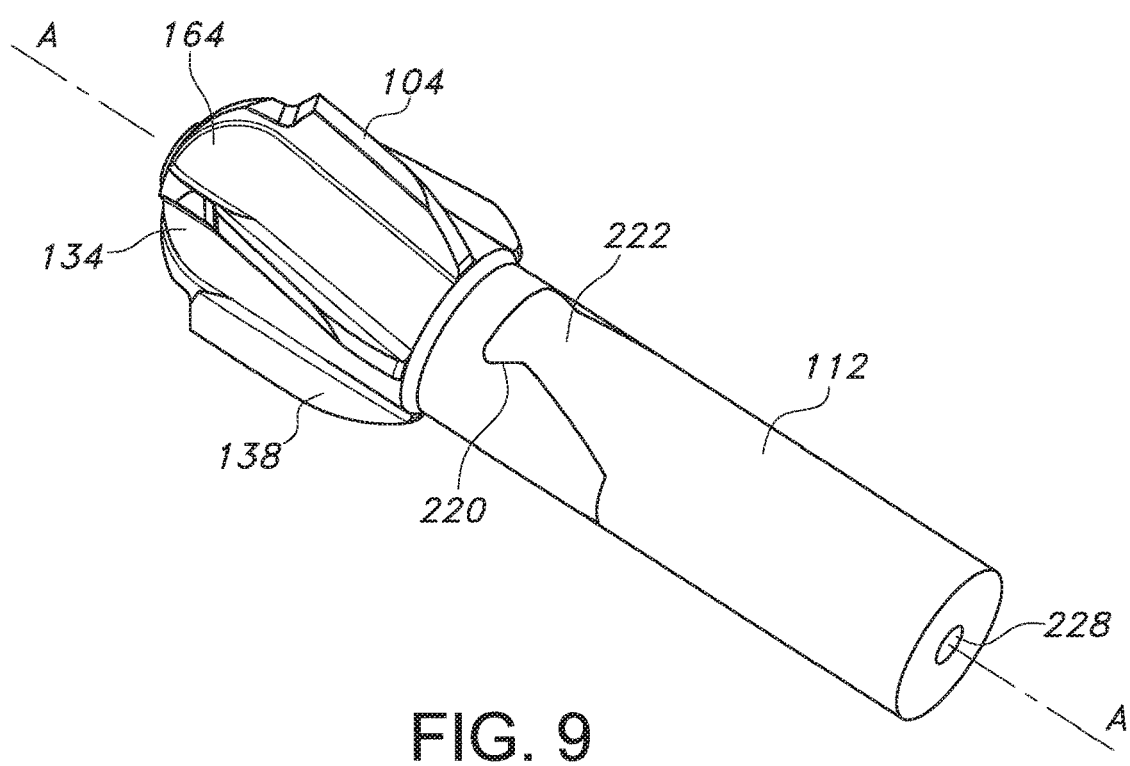

FIGS. 8 and 9 illustrate an embodiment of a shaft attachment interface 218 which may be used to attach the drive shaft 112 to the cutting head 100. In an embodiment, a lumen 228 may extend along the longitudinal axis A-A through the shaft 112, thus allowing debris to exit from the cutting head lumen 124 through the shaft 112. As illustrated, the shaft attachment interface 218 may comprise a cutout portion 220 that is designed to receive a projection 222 having a corresponding cross-sectional shape in a keyed mated interface. In an embodiment, the projection 216, constructed at the distal shaft end, is designed to be received within a cutout portion 220 having a corresponding cross-sectional shape, within a portion of the barrel 108. The projection 222 may be received within the cutout portion 220 in a dovetail relationship. In the embodiment shown in FIG. 8, the cutout portion 220 may comprise at least one groove 224 that is formed within the sidewall of the barrel 108 extending perpendicular to the longitudinal axis A-A. A ridge 226 that corresponds to the dimension of the groove 224 outwardly extends from the distal shaft end. As shown in FIG. 9, the ridge 226 formed at the distal end of the drive shaft is received within the groove 224 formed within the barrel sidewall in a mated dovetail relationship.

In an embodiment, the cutout portion 220 and the corresponding shaped projection 222 are not limited to the embodiment illustrated in FIGS. 8 and 9. It is further contemplated that the cutout portion 220 formed within the barrel portion 108 may be constructed of a plurality of non-limiting shapes such that the distal shaft end is formed of a corresponding shape that is capable of being received in a mated relationship therewithin. For example, the cutout portion 220 may be of a cross-sectional shape having a curved geometry, a rectangle geometry, triangular geometry or star geometry. It is also contemplated that that cutout portion 220 may be formed within the distal shaft end and the corresponding shaped projection 222 is formed at the barrel 108 of the cutting head.

In an embodiment, the cutting head 100 may be formed having a unitary body construction. In a preferred embodiment, the cutting head 100 may be formed using a metal injection molding process in which powdered metal such as 17-4 stainless steel mixed with a binder material is injected into a mold that defines the cutting head shape. After the shape of the cutting head is formed within the mold, the molded part is then heat treated at a temperature ranging from about 100° C. to about 500° C. While 17-4 stainless steel is a preferred material in which the cutting heads are formed, the cutting heads may also be formed from other metallic material such as, but not limited to, ferrous alloys, aluminum, precious metals, titanium alloys, nickel, nickel-base super alloys, molybdenum, molybdenum-copper, tungsten alloys, cobalt-chromium, carbides, and cermets such as Fe—TiC. In addition, the cutting head 100 may also be formed from polymeric material materials, such as but are not limited to, polyetheretherketone (PEEK), polyacrylamide (PARA) and acrylonitrile butadiene styrene (ABS).

Thus, it has been shown that the reamer cutting head of the present invention provides for a low cost flexible single use intramedullary cutting tool. The present invention does not require additional grinding or re-sharpening procedures which ensure optimal sharpness and sterilization. The features of the present invention provide for an efficient intramedullary cutting tool with an optimized cutting design that enhances reaming efficiency and effectiveness.

What is claimed is:

1. A bone cutter, comprising:
   a) a proximal barrel portion configured for detachable connection to a source of rotary motion;
   b) a cutting head body extending along a longitudinal axis from a proximal end of the barrel portion to a distal end surface, wherein the distal end surface is of a convex geometry outwardly extending in a distal direction; and
   c) at least two spaced apart cutting blades supported by the cutting head body, each cutting blade comprising opposing leading and trailing sidewall surfaces, wherein a relief surface resides between the leading and trailing sidewall surfaces, and wherein a tissue cutting edge resides at an intersection of the leading sidewall surface and the relief surface along at least a portion of each of the at least two cutting blades.

2. The bone cutter of claim 1 wherein the leading sidewall surface has a leading sidewall height that is greater than a trailing sidewall height of the trailing sidewall surface along at least a portion of each of the at least two cutting blades.

3. The bone cutter of claim 1 wherein each cutting blade comprises a nose blade segment that extends from the distal end surface to a primary blade segment, the primary blade segment extending to a proximal blade segment, and wherein the proximal blade segment extends in a proximal direction towards the proximal barrel portion.

4. The bone cutter of claim 3 wherein, along any one cross-section taken from a distal end of the primary blade segment to a proximal end of the primary blade segment, the one cross-section being aligned normal to the longitudinal axis and intersecting an outermost endpoint of the cutting surface:
   i) a first imaginary line is coincident with the blade relief surface;
   ii) a second imaginary line intersects the longitudinal axis and the outermost endpoint of the cutting surface;
   iii) a third imaginary line is normal to the second imaginary line and intersects the outermost endpoint of the cutting surface; and
   iv) wherein the blade relief angle is defined between the first and third imaginary lines and ranges from about 25° to about 35°.

5. The bone cutter of claim 3 wherein, along any one cross-section taken from the distal end of the proximal blade segment to a proximal end of the proximal blade segment, the one cross-section being aligned normal to the longitudinal axis and intersecting an outermost endpoint of the cutting surface:
   i) a first imaginary line that is coincident with the blade relief surface;
   ii) a second imaginary line intersecting the longitudinal axis and the outermost endpoint of the cutting surface;
   iii) a third imaginary line that is normal to the second imaginary line and intersects the outermost endpoint of the cutting surface; and
   iv) wherein the blade relief angle is defined between the first and third imaginary lines and ranges from about 25° to about 35°.

6. The bone cutter of claim 4 wherein, along any one cross-section taken from the distal end of the primary blade segment to the proximal end of the primary blade segment, the one cross-section being aligned normal to the longitudinal axis and intersecting an outermost endpoint of the cutting surface:
   i) a fourth imaginary line coincident with the cutting surface and intersects the outermost endpoint of the cutting surface; and
   ii) wherein the rake relief angle is defined between the second and fourth imaginary lines and ranges from about 2° to about 8°.

7. The bone cutter of claim 5 wherein, along any one cross-section taken from the distal end of the proximal blade segment to the proximal end of the proximal blade segment, the one cross-section being aligned normal to the longitudinal axis and intersecting an outermost endpoint of the cutting surface:
   i) a fourth imaginary line coincident with the cutting surface and intersects the outermost endpoint of the cutting surface; and
   ii) wherein the rake relief angle is defined between the second and fourth imaginary lines and ranges from about 2° to about 8°.

8. The bone cutter of claim 3 wherein a transition segment comprising a flat and a notch resides between the nose and primary blade segments, wherein the flat extends in a proximal direction from a proximal end of the nose blade segment and the notch extends in a proximal direction from a proximal end of the flat to a distal end of the primary blade segment.

9. The bone cutter of claim 8 wherein the notch has a surface that is at least partially recessed within the blade relief surface.

10. The bone cutter of claim 3 wherein a primary blade segment angle extends between a first imaginary line that is coincident with the tissue cutting edge along the flat blade segment and a second imaginary line coincident to the tissue cutting edge along the primary blade segment, wherein the primary segment angle is obtuse.

11. The bone cutter of claim 3 wherein a deflection angle extends between a first imaginary line that is coincident with the intersection of the leading sidewall surface and relief surface along the proximal blade segment and a second imaginary line that is coincident with the intersection of the leading sidewall surface and relief surfaces along the nose segment, wherein the deflection angle ranges from about 5° to about 15°.

12. The bone cutter of claim 1 wherein a lumen extends along the longitudinal axis through the body distal end and at least partially through the body.

13. The bone cutter of claim 1 wherein a blade width extends between the opposing leading and trailing sidewall surfaces, wherein the blade width ranges from 0.1 cm to about 0.5 cm.

14. The bone cutter of claim 1 wherein the barrel portion comprises a cutout having a cross-sectional geometry oriented perpendicular to the longitudinal axis that at least partially extends through the annular sidewall, wherein the cutout portion is configured to receive a projection formed at an end of a drive shaft in a removably mated relationship.

15. The bone cutter of claim 1 wherein a sleeve comprising a collar having a collar distal end with a first collar outer diameter at a sleeve distal end extends along the longitudinal axis to a collar proximal end having a second outer diameter, a tube portion extending from the collar proximal end along the longitudinal axis to a sleeve proximal end, wherein the first collar outer diameter is greater than the second collar outer diameter.

16. The bone cutter of claim 1 having a unitary body construction.

17. The bone cutter of claim 1 further composed of a material selected from the group consisting of stainless steel, a ferrous alloy, aluminum, a precious metal, titanium, a titanium alloy, nickel, a nickel alloy, molybdenum, a molybdenum-copper alloy, tungsten, a tungsten alloy, a cobalt-chromium alloy, and a carbide.

18. A bone cutter, comprising:
  a) a body comprising an annular outer surface extending along a longitudinal axis from a body proximal end to a body distal end;
  b) at least two spaced apart blades, each blade comprising:
    i) opposing leading and trailing blade sidewall surfaces that outwardly extend from the annular surface, a relief blade surface therebetween, wherein the relief blade surface extends from a blade distal end located at the body distal end to a blade proximal end that resides distal of the body proximal end;
    ii) a tissue cutting edge extending along at least a portion of the blade, wherein the tissue cutting edge is formed at the intersection of the leading sidewall surface and the relief surface;
    iii) a primary blade segment and a proximal blade segment positioned between a nose blade segment and a trailing blade segment, wherein the nose blade segment is positioned distal the primary blade segment, the primary blade segment positioned distal the proximal blade segment, and the proximal blade segment positioned distal the trailing blade segment, and wherein the relief blade surface extends from the nose blade segment to the trailing blade segment; and c) wherein the tissue cutting edge extending along the primary blade segment is oriented at a relief angle that ranges from 10° to 60°.

19. The bone cutter of claim 18 wherein the nose blade segment is of a convex shape outwardly extending in a distal direction.

20. The bone cutter of claim 18 wherein the tissue cutting edge along the primary blade segment has a rake angle that ranges from 2° to 10°.

21. The bone cutter of claim 18 wherein the orientation of the relief surface along the proximal blade segment deviates from the orientation of the relief surface along the nose blade segment, wherein the deflection angle is the angle that spans between the intersection of a first imaginary line coincident with the intersection of the leading sidewall surface and the relief surface along the proximal blade segment and a second imaginary line coincident with the intersection of the leading sidewall surface and the relief surface along the nose blade segment, and wherein the deflection angle ranges from about 5° to about 15°.

22. The bone cutter of claim 18 wherein the leading sidewall surface has a leading sidewall height that is greater than a trailing sidewall height of the trailing sidewall surface along at least a portion of each of the at least two cutting blades.

23. The bone cutter of claim 18 wherein a transition blade segment is positioned between the nose blade segment and the primary blade segment, wherein the transition blade segment comprises a flat positioned distal a notch, and wherein the notch comprises a surface that is at least partially recessed within the relief surface.

24. The bone cutter of claim 18 wherein a lumen extends along the longitudinal axis through the body distal end and at least partially through the body.

25. The bone cutter of claim 18 wherein a blade width extends between the opposing leading and trailing sidewall surfaces, wherein the blade width ranges from 0.1 cm to about 0.5 cm.

26. The bone cutter of claim 18 having a unitary body construction.

27. The bone cutter of claim 18 wherein a barrel portion having an annular sidewall that defines a cavity therewithin extends from the blade proximal end, wherein the cavity is configured to removably receive a drive shaft.

28. The bone cutter of claim 27 wherein the barrel portion comprises a cutout having a cross-sectional geometry oriented perpendicular to the longitudinal axis, wherein the cutout extends at least partially through the annular sidewall, and wherein the cutout is configured to receive a projection formed at an end of a drive shaft in a removably mated relationship.

29. The bone cutter of claim 18 wherein a sleeve comprising a collar having a collar distal end with a first collar outer diameter at a sleeve distal end extends along the longitudinal axis to a collar proximal end having a second outer diameter, a tube portion extending from the collar proximal end along the longitudinal axis to a sleeve proximal end, wherein the first collar outer diameter is greater than the second collar outer diameter.

30. The bone cutter of claim 18 further composed of a material selected from the group consisting of stainless steel, a ferrous alloy, aluminum, a precious metal, titanium, a titanium alloy, nickel, a nickel alloy, molybdenum, a molybdenum-copper alloy, tungsten, a tungsten alloy, a cobalt-chromium alloy, and a carbide.

* * * * *